(12) United States Patent
Kaus et al.

(10) Patent No.: US 9,757,588 B2
(45) Date of Patent: Sep. 12, 2017

(54) DEFORMABLE REGISTRATION OF IMAGES FOR IMAGE GUIDED RADIATION THERAPY

(75) Inventors: Michael Kaus, Toronto (CA); Vladimir Pekar, Hamburg (DE); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1989 days.

(21) Appl. No.: 12/300,339

(22) PCT Filed: May 1, 2007

(86) PCT No.: PCT/US2007/067846
§ 371 (c)(1),
(2), (4) Date: Nov. 11, 2008

(87) PCT Pub. No.: WO2007/133932
PCT Pub. Date: Nov. 22, 2007

(65) Prior Publication Data
US 2009/0187422 A1    Jul. 23, 2009

Related U.S. Application Data

(60) Provisional application No. 60/746,999, filed on May 11, 2006.

(51) Int. Cl.
*G06Q 10/00*    (2012.01)
*A61N 5/10*    (2006.01)
(Continued)

(52) U.S. Cl.
CPC .............. *A61N 5/103* (2013.01); *A61B 6/466* (2013.01); *G06F 19/3481* (2013.01);
(Continued)

(58) Field of Classification Search
USPC ........ 250/363.04; 378/8, 150, 108; 600/407, 600/426
See application file for complete search history.

(56) References Cited

U.S. PATENT DOCUMENTS 6,208,712 B1 *    3/2001    Hernandez-Guerra ....... 378/150
7,010,164 B2    3/2006    Weese et al.
(Continued)

FOREIGN PATENT DOCUMENTS

| EP | 1521056 A2 | 4/2005 |
|---|---|---|
| WO | 2005031629 A1 | 4/2005 |
| WO | 2006131848 A2 | 12/2006 |

OTHER PUBLICATIONS

Bulow, T., et al.; A General Framework for Tree Segmentation and Reconstruction from Medical Volume Data; 2004; Lecture Notes in Computer Science; 3216; pp. 533-540.
(Continued)

*Primary Examiner* — Valerie Lubin

(57) ABSTRACT

A system and method for developing radiation therapy plans and a system and method for developing a radiation therapy plan to be used in a radiation therapy treatment is disclosed. A radiation therapy plan is developed using a registration of medical images. The registration is based on identifying landmarks located within inner body structures.

19 Claims, 2 Drawing Sheets

(51) Int. Cl.
 A61B 6/00 (2006.01)
 G06Q 50/22 (2012.01)
 G06T 7/33 (2017.01)
 G06T 7/38 (2017.01)
 A61B 5/00 (2006.01)
 A61B 6/03 (2006.01)
 A61B 8/00 (2006.01)
 G06F 19/00 (2011.01)

(52) U.S. Cl.
 CPC ............... *G06Q 50/22* (2013.01); *G06T 7/33* (2017.01); *G06T 7/38* (2017.01); *A61B 5/7285* (2013.01); *A61B 6/03* (2013.01); *A61B 6/541* (2013.01); *A61B 8/543* (2013.01); *A61N 5/1037* (2013.01); *A61N 2005/1061* (2013.01); *G06F 19/321* (2013.01); *G06F 19/3437* (2013.01); *G06T 2207/30004* (2013.01)

(56) References Cited

U.S. PATENT DOCUMENTS

| | | | |
|---|---|---|---|
| 7,298,879 | B2 | 11/2007 | Wiemker |
| 2005/0018891 | A1 | 1/2005 | Barfuss et al. |
| 2005/0205792 | A1* | 9/2005 | Rousso et al. ........... 250/363.04 |
| 2006/0020195 | A1* | 1/2006 | Falco et al. .................. 600/407 |
| 2006/0094951 | A1* | 5/2006 | Dean et al. .................. 600/407 |
| 2006/0147114 | A1 | 7/2006 | Kaus et al. |
| 2007/0053482 | A1* | 3/2007 | Kohler et al. .................... 378/8 |
| 2007/0179377 | A1* | 8/2007 | Carlsen et al. .............. 600/407 |
| 2008/0262345 | A1* | 10/2008 | Fichtinger et al. ........... 600/426 |

OTHER PUBLICATIONS

Haker, S., et al.; Landmark-Guided Surface Matching and Volumetric Warping for Improved Prostate Biopsy Targeting and Guidance; 2004; LNCS; 3216; pp. 853-861.
Keall, P. J., et al.; Four-dimensional radiotherapy planning for DMLC-based respiratory motion tracking; 2005; Med. Phys.; 32(4)942-951.
Keall, P.; 4-Dimensional Computed Tomography Imaging and Treatment Planning; 2004; Seminars in Radiation Oncology; 14(1)81-90.
Li, B., et al.; 3-D Inter-Subject Warping and Registration of Pulmonary CT Images for a Human Lung Model; 2002; Medical Imaging Proc. SPIE; 4683; pp. 324-335.
Mitsa, T., et al.; Image Registration Using Elastic Contours and Internal Landmarks; 1998; IEEE Instrumentation and Measurement Conf.; pp. 451-455.
Rietzel, E., et al.; Four-Dimensional Image-Based Treatment Planning: Target Volume Segmentation and Dose Calculation in the Presence of Respiratory Motion; 2005; Int. J. Radiation Oncology Biol. Phys.; 61(5)1535-1550.
Pan, T., et al.; 4D-CT imaging of a volume influenced by respiratory motion on multi-slice CT; 2004; Med. Phys.; 31(2)333-340.
Schlesinger, D. J., et al.; Segmentation of cortical surface and interior brain structures using active surface/active volume templates; 1997; Medical Imaging Proc. SPIE; 3034; pp. 252-264.
Zagrodsky, V., et al.; Registration-Assisted Segmentation of Real-Time 3-D Echocardiographic Data Using Deformable Models; 2005; IEEE Trans. on Medical Imaging; 24(9)1089-1099.
Roesch, P., et al.; 3D Respiratory Motion Compensation by Template Propagation; 2002; Lecture Notes in Computer Science; 2489:639-646.

* cited by examiner

DEFORMABLE REGISTRATION OF IMAGES FOR IMAGE GUIDED RADIATION THERAPY

CROSS REFERENCE TO RELATED APPLICATIONS

This application claims the benefit of U.S. provisional application Ser. No. 60/746,999 filed May 11, 2006, which is incorporated herein by reference.

Radiotherapy is the treatment of diseases, such as cancer tumors, with radiation, such as X-ray radiation. In the course of administering radiation to the diseased tissue, some healthy tissue is also exposed to the radiation. Exposure of healthy tissue to radiation can cause treatment related complications. As such, it is desirable to accurately and precisely contour the diseased region so that the radiation is applied predominately to the diseased tissue and minimally to the surrounding healthy tissue.

An accurate and precise contour of the treated region (the planning target volume or PTV) incorporates the motion of the target during fractionated treatment. Motion can be physical movement of the patient (setup error) or movement and deformation of the internal tissues, including the diseased tissue, caused by physiological functions, such as cardiac, respiratory, and digestive systems, or as a result of treatment response. In conventional treatment planning, the PTV is based on statistics of patient populations, resulting in too large or inaccurate target areas. In order to assess patient-specific motion, a series of images is taken over a period of time to get a 3D description of the geometric change of the diseased tissue and surrounding organs. The temporal sampling can be seconds to monitor e.g. breathing motion using 4D gated imaging, or days and weeks, or combinations of these such as weekly imaging using a 4D gated imaging technique. Integrating time-samples of 3D images in radiotherapy is generally termed image-guided radiotherapy (IGRT) or adaptive radiotherapy. Such adjustment allows for application of radiation to a more precise target region.

To accumulate a 4D dose-volume histogram, the spatial correspondences between the volume elements of the organs at risk and the target need to be calculated. Voxel-based registration methods are difficult to apply due to lack of gray-value correspondence. Surface-based methods, which deform triangular meshes to the objects of interest, have successfully been used to segment anatomical structures. In such methods, the vertices of the adapted meshes define corresponding landmarks between object surfaces. This enables a deformation field for all voxels in the image to be estimated by elastic point-based registration methods.

If motion inside the imaged object is not well correlated to the motion on its surface, interpolating a motion field based on the surface alone will result in incorrect motion estimates. For example, in imaging the lungs, the motion from the diaphragm, the heart and the chest wall result in complex motions of the lung lobes. In addition, depending on the position of the tumor or of region of interest, which may or may not be attached to the lung wall, and the tissue properties of the tumor, e.g. quasi-solid or soft, the tumor motion may or may not correlate well with the lung and/or heart surface.

Proper motion compensation is important in radiation therapy planning as it allows for organ contours to be properly delineated. Furthermore, it allows for the correct computation of radiation dose. Consequently it is desired to develop a method for radiation therapy planning that will accurately account for motion of an imaged object to allow for the development of a highly precise radiation therapy plan, and hence treatment.

The present invention is directed to a system and method for developing radiation therapy plans and a system and method for developing a radiation therapy plan to be used in a radiation therapy treatment. A radiation therapy plan is developed using a registration of medical images. The registration is based on identifying landmarks located within inner body structures.

In the accompanying drawings, which are incorporated in and constitute a part of this specification, embodiments of the invention are illustrated, which, together with a general description of the invention given above, and the detailed description given below serve to illustrate the principles of this invention. One skilled in the art should realize that these illustrative embodiments are not meant to limit the invention, but merely provide examples incorporating the principles of the invention.

The system and method disclosed herein provides for registration of images such as to account for movement of the imaged object. Such a system and method allows for precise radiation therapy planning and treatment.

Figure 1:
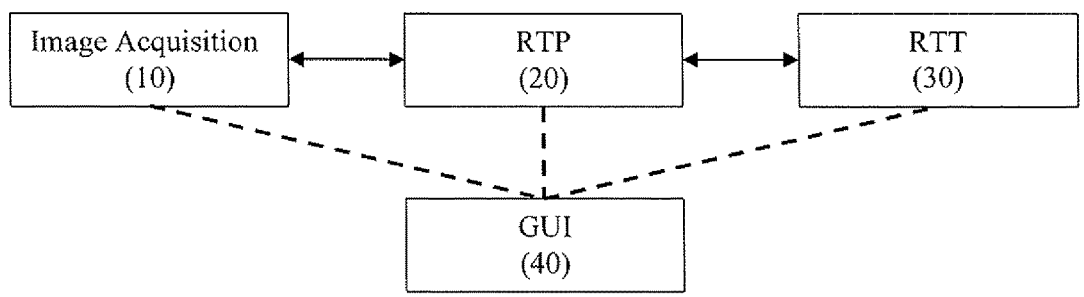
FIG. 1 illustrates a block diagram of a radiation therapy planning and treatment system.

FIG. 1 illustrates a block diagram of an illustrative example of a system of the present invention. The system includes an image acquisition component 10, a radiation therapy planning component (RTP) 20, a radiation therapy treatment component (RTT) 30, and a graphical user interface (GUI) 40. It should be appreciated that the system shown in FIG. 1 is merely an illustrative example and thus should not be limit the scope of this disclosure. For example, some systems may not include the RTT component 30 and/or the GUT 40. In some systems the GUI 40, shown as interfacing with all three of the other components, may only interface with one or two of the other components.

The image acquisition component 10 can be any imaging system, such as, for example, a CT system, an X-Ray system, a nuclear imaging system, an ultrasound system, a MR system, or any combination thereof. Preferably the system allows for gated imaging information to be gathered and passed on to the RTP component 20. In some embodiments, the image acquisition component 10 is located remote from the RTP component 20, or other components. In this regard the information gathered from the image acquisition component 10 can be delivered to the other components via a network connect or via a data storage medium. In addition, the image acquisition can occur within the same relative time frame as the development of the radiation therapy plan, or the image acquisition can occur at any time prior to the development of the radiation therapy plan. Additionally, any method of image acquisition can be used. For example, methods of obtaining 4D CT data are disclosed in Pan et al., MedPhys 31(2):333-340 (2004), the entire disclosure of which is hereby incorporated by reference.

The RTP component 20 can be a general processor and a specialized processor with RTP software loaded onto or embedded into the processor. The RTT component 30 can be any treatment delivery device, such as, for example, a linear accelerator. The GUI 40 can consist of any input and/or output device or any combination thereof. For example the GUI may include a monitor, a keyboard, a data storage device, a data storage access device, a data network or any other component to help a radiation therapy technician interact with the other components to acquire image data, plan radiation therapy, and/or deliver radiation therapy to a subject.

Figure 2:
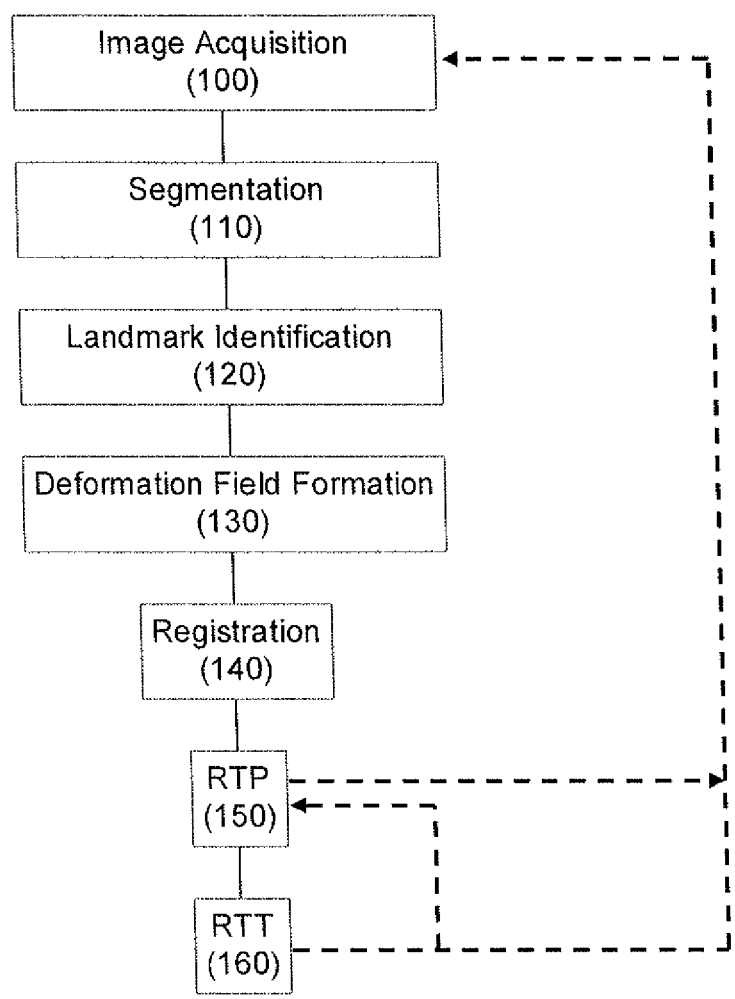
FIG. 2 illustrates a flow diagram of a radiation therapy planning and treatment process.

FIG. 2 illustrates a method of delivering radiation therapy. It should be appreciated that the method can be limited to forming the radiation therapy plan or a fraction of the radiation therapy treatment. The embodiment that is shown starts with the acquisition of imaging data at 100. This can be done using the image acquisition component 10 mentioned above. The image data is preferably 4D CT data. The image data is then relayed to the RTP component 20, where it is segmented into different structures. As shown at 110, segmentation of the structures, e.g. a tumor and/or organs at risk, can be accomplished using a model-based segmentation or alternative segmentation approaches. The structures of interest are represented with a triangular surface mesh, either directly if a model-based segmentation is used or after triangulation of the segmentation. Methods of segmentation are disclosed in U.S. Pat. No. 7,010,164 entitled Image Segmentation which granted on Mar. 7, 2006 and U.S. Patent Application No. 60/597,087 entitled Automated Stool Removal Method for Medical Imaging, filed Nov. 9, 2005, the entire disclosures of which are hereby incorporated by reference.

Landmarks on the surface of the volume of interest are given by the vertices of the triangular surface meshes. Methods of calculating a volumetric deformation field based on triangular surface meshes alone are disclosed in U.S. Patent Application 60/595,122 entitled Point Subselection For Past Deformable Point-Based Imaging, filed Jun. 8, 2005, the entire disclosure of which is hereby incorporated by reference.

Landmarks inside the volume of interest are then identified, shown at 120. The identification of the landmarks inside the volume of interest can be done using any one, or any combination, of a template-matching algorithm, an automated vessel tree extraction algorithm, an automated marker detection algorithm. A method of using a template-matching algorithm is disclosed in Roesch et al., 3D Respiratory Motion Compensation by Template Propagation MICCAI 2002, Lecture Notes in Computer Science 2489 (2002) 639-646, the entire disclosure of which is hereby incorporated by reference. In such a method, points with similar grey value characteristics are identified inside a volume of interest defined by corresponding surface meshes. An approach such as this is typically fast in that it is restricted in its search to volumes of interest.

An automated vessel tree extraction algorithm is disclosed in Buelow et al., A General Framework For Tree Segmentation and Reconstruction Form Medical Volume Data, NICCAI 2004, the entire disclosure of which is hereby incorporated by reference. In such a method, a first order vessel bifurcation in corresponding structures is extracted. Using the topology of the vessel trees, corresponding bifurcations can be identified in both image datasets, and the respective coordinates used as corresponding landmarks. Methods such as these are most applicable to identification of landmarks in the lungs or the liver.

In the case that markers are used for patient setup correction, such as, for example, gold markers used in the prostate, an algorithm for automated detection can be used to identify additional corresponding points inside the volume of interest. In addition, combinations of these methods can be used, or alternatively other landmark identification algorithms and/or methods can also be used.

The segmentation and landmark identification is used to establish a deformation field at 130. The formation of a deformation field, allows for registration of images, as shown at 140. An example of the formation of a deformation field and the subsequent registration of images is disclosed in co-pending U.S. patent application Ser. No. 10/573,730, entitled Method and Device for Planning Radiation Therapy, filed Mar. 28, 2006 and U.S. Patent Application No. 60/597,087 entitled Automated Stool Removal Method for Medical Imaging, filed Nov. 9, 2005, the entire disclosures of which are hereby incorporated by reference.

Once the images are registered, a radiation therapy plan (RTP) can be established, shown at 150. The radiation therapy plan allows for accurate organ contouring and dose calculation. The dose calculation can be determined for each dataset, and then subsequently accumulated into a single dataset. This allows for the full dose to be distributed properly and can allow for further optimization of the treatment plan. Once a RTP has been established, a radiation therapy treatment session (RTT) can take place, shown at 160. Alternatively, the process can loop back and take further images in order to further develop the RTP. Also, the RTP and RTT can occur at different times and/or at different sites. Consequently, a method, such as that shown in FIG. 2, can be contained solely within the 100-150 loop, thereby allowing for the RTT to take place at a different time and/or location. In such cases, the RTP can be periodically update, as often as desired, with additional image acquisition data and subsequent processing.

For methods that include the RTT, the process can either be complete after the RTT or it can loop back, such as in the case of fractionated treatments. In methods that allow for treatment loops, after the RTT at 160, the process can return to the RTP 150, which will be used for the next fraction of the RTT. In such cases the next fraction of RTT may use the same dose distribution as previously applied or may be different as established in the initial RTP. For example, the first fraction of treatment may be a full dose, while the second fraction may be a percentage of the full dose. In other methods, after the RTT, the process returns to the image acquisition phase and, through the subsequent processing, refines or redefines the RTP. Some methods can switch between returning to the RTP and the image acquisition, depending on a certain number of fractions (e.g. every other or every third), a certain time period (e.g. every five days), a projected or actual change in size and/or shape of the target, the desire of the technician or doctor, or any other basis.

The invention has been described with reference to one or more preferred embodiments. Clearly, modifications and alterations will occur to other upon a reading and understanding of this specification. It is intended to include all such modifications and alterations insofar as they come within the scope of the appended claims or equivalents thereof.

The invention claimed is:
1. A radiation therapy planning procedure comprising:
   a) with one or more processors, segmenting organs and diseased tissue with surface meshes from 4D medical images received from a diagnostic imaging device and from a computer memory;
   b) identifying surface and internal landmarks located within one or more of the segmented organs and diseased tissue, the surface landmarks including vertices of the surface meshes and the internal landmarks being identified by at least one of:

a template matching algorithm;
an automated vessel tree extraction algorithm; and
an automated marker detection algorithm;
c) determining a deformation field based on the identified surface and internal landmarks;
d) applying the deformation field to register the 4D medical images;
e) developing a radiation therapy plan based on the registered 4D medical images; and
f) on a display device, displaying at least one of the 4D medical images, the registered 4D medical images, and the developed radiation therapy plan.

2. The radiation therapy planning procedure of claim 1 wherein the 4D medical images include 4D CT images.

3. The radiation therapy planning procedure of claim 1, further comprising:
after radiation treatment with the developed radiation therapy plan, acquiring an additional 4D medical image;
repeating steps a)-d) using the additional 4D medical image; and
refining the radiation therapy plan using a change in shape, location, and/or volume of the segmented organs and target areas to calculate a new planned dosage to each organ and diseased tissue and accumulate a refined radiation therapy plan.

4. The radiation therapy planning procedure of claim 1 wherein identifying landmarks includes:
implementing an automatic vessel-tree extraction algorithm.

5. The radiation therapy planning procedure of claim 1 further including:
with a linear accelerator, delivering a radiation treatment fraction in accordance with the refined radiation therapy plan.

6. The radiation therapy planning procedure of claim 5 wherein refining the radiation therapy plan includes:
determining a cumulative radiation dose distribution over a plurality of radiation treatment factions.

7. The radiation therapy planning procedure of claim 6 wherein determining the cumulative radiation dose distribution includes:
determining a first dose for a target area and a second dose for each of one or more other regions of interest.

8. The radiation therapy planning procedure of claim 1 further comprising:
on a graphical user interface, verifying on at least one of the segmented 4D medical images, the identified landmarks, and the registered 4D medical images.

9. A radiation therapy planning system comprising:
one or more processors programmed to:
segment a first medical image received from a diagnostic scanner and a second medical image received from computer memory to identify anatomical internal body structures with a surface mesh;
identify surface and internal landmarks, the surface landmarks given by vertices of the surface meshes, and the internal landmarks being located within an interior of at least one of the identified internal body structures by at least one of:
a template matching algorithm;
an automated vessel tree extraction algorithm; and
an automated marker detection algorithm;
calculate a deformation field which brings the identified surface and internal landmarks in the first and second medical images into registration;
apply the calculated deformation field to register the medical images; and
establish a radiation dose distribution in the internal body structures using the registered medical images.

10. The radiation therapy planning system of claim 9 wherein the landmarks are identified using a template-matching algorithm.

11. The radiation therapy planning system of claim 9 wherein the landmarks are identified using an automatic extraction of vessel-trees algorithm.

12. The radiation therapy planning system of claim 9 wherein the one or more processors identify additional landmarks that are not within one of the internal anatomical body structures.

13. A radiation therapy treatment procedure comprising:
with one or more processors:
segmenting a first medical image to define surfaces of internal body structures with surface meshes;
identifying internal landmarks located internal to one of the internal body structures segmented with surface meshes and locating surface landmarks of a surface of the one body structure segmented with the surface meshes;
calculating a deformation field to the first medical image based on the identified internal and surface landmarks;
applying the deformation field to the first medical image to register the first medical image;
forming a radiation therapy plan;
with a linear accelerator:
performing a first fractional treatment in which a radiation beam is directed through the one of the internal body structures;
with one or more processors:
segmenting a second medical image to define surfaces of internal body structures with surface meshes;
identifying internal landmarks located internal to the one internal body structure segmented with surface meshes in the second image and locating surface landmarks of the surface of the one body structure segmented with surface meshes in the second image;
calculating a deformation field to the second medical image based on the identified internal and surface landmarks;
applying the calculated deformation field to the second medical image to register the second medical image;
refining the radiation therapy plan based on the differences between the deformation fields of the registered medical images; and
with a linear accelerator:
performing a second fractional treatment in which a radiation beam is directed through the one of the internal body structures; and
with one or more processors:
computing a radiation dose received by the one of the body structures in the first and second fractions.

14. The radiation therapy treatment procedure of claim 13 wherein the internal landmarks are identified using a template-matching algorithm.

15. The radiation therapy treatment procedure of claim 13 wherein the internal landmarks are identified using an automatic extraction of vessel-trees algorithm.

16. The radiation therapy treatment procedure of claim 13 wherein the landmarks are internal anatomical structures located interior to one or more of the internal body structures.

17. The radiation therapy treatment procedure of claim 13 wherein the medical images include 4D CT images.

18. A non-transitory, computer readable medium carrying software which controls one or more processors to:
  segment medical images based on surfaces of internal body structures with triangular meshes;
  identify surface landmarks from vertices of the triangular meshes and internal landmarks within at least one of the internal body structures;
  calculate a deformation field based on the identified surface and internal landmarks which brings the medical images into registration;
  apply the calculated deformation field to the medical images to register the medical images; and
  form a radiation therapy plan based on the registered medical images.

19. The radiation therapy planning treatment system of claim 9 further comprising:
  a graphical user interface for viewing at least one of:
    the radiation therapy plan;
    intermediate images representative of segmented medical images;
    the identified surface landmarks;
    the identified internal landmarks;
    graphical representation of the calculated deformation field; and
    the registered medical images.

* * * * *